United States Patent [19]

Spivack et al.

[11] Patent Number: 4,559,379
[45] Date of Patent: Dec. 17, 1985

[54] 4-HYDROXYPHENYLTHIO SUBSTITUTED STABILIZERS FOR POLYMERS

[75] Inventors: John D. Spivack; Stephen D. Pastor, both of Spring Valley, N.Y.

[73] Assignee: Ciba Geigy Corporation, Ardsley, N.Y.

[21] Appl. No.: 698,278

[22] Filed: Feb. 5, 1985

Related U.S. Application Data

[63] Continuation of Ser. No. 531,876, Sep. 14, 1983, abandoned.

[51] Int. Cl.$^4$ .................. C08K 5/36; C07C 149/40
[52] U.S. Cl. .................... 524/289; 560/17
[58] Field of Search .................. 524/289; 560/17

[56] References Cited

U.S. PATENT DOCUMENTS

| | | | |
|---|---|---|---|
| 3,285,855 | 11/1966 | Dexter et al. | 524/291 |
| 3,466,323 | 9/1969 | Tholstrup et al. | 524/231 |
| 3,536,661 | 10/1970 | Hagemeyer et al. | 560/17 |
| 3,832,329 | 8/1968 | Geering et al. | 528/190 |
| 3,951,915 | 4/1976 | Keck et al. | 528/195 |
| 3,989,664 | 11/1976 | Kawase et al. | 524/291 |
| 4,097,350 | 6/1978 | Pastor et al. | 204/159.23 |
| 4,308,195 | 12/1981 | Mayer et al. | 524/114 |
| 4,311,637 | 1/1982 | Cottman | 560/17 |
| 4,394,476 | 7/1983 | Cottman | 560/289 |

FOREIGN PATENT DOCUMENTS

79855AI  5/1983  European Pat. Off.
49-75551  7/1974  Japan .

OTHER PUBLICATIONS

Chemical Abstracts, vol. 86 (1977) 5066m.

Primary Examiner—Veronica P. Hoke
Attorney, Agent, or Firm—Luther A. R. Hall; Harry Falber

[57] ABSTRACT

The title compounds correspond to the formula

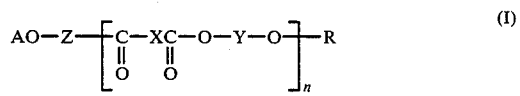

where n is 1 and are characterized in that at least one of A, X or Y contains a group of formula

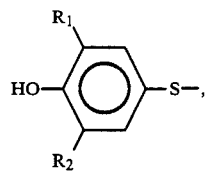

these compounds being useful as stabilizers for organic polymers and lubricating oils to counteract the degradative effects of heat, light and air.

6 Claims, No Drawings

4-HYDROXYPHENYLTHIO SUBSTITUTED STABILIZERS FOR POLYMERS

This is a continuation of application Ser. No. 531,876, filed Sept. 14, 1983, now abandoned.

Organic polymeric materials such as plastics and resins, and lubricating and mineral oils are subject to thermal, oxidative and photo-degradation. A great variety of stabilizers are known in the art for stabilizing a diversity of substrates. Their effectiveness varies depending upon the causes of degradation and the substrate stabilized. In general, it is difficult to predict which stabilizer will be most effective and most economical for any one area of application. For example stabilizer effectiveness in reducing volatility may depend upon preventing bond scission in the substrate molecule. Limiting embrittlement and retaining elasticity in a polymer or rubber may require prevention of excessive crosslinking and/or chain scission. Prevention of discoloration may require inhibiting reactions which yield new chromophores or color bodies in the substrate or stabilizer. Problems of process stability and incompatibility must also be considered.

It has now been determined that the polymeric 4-hydroxyphenylthio compounds of this invention possess an unusual combination of desirable properties which make them particularly effective and useful as stabilizers. The compounds are particularly effective in protecting polyolefins, high impact polystyrene, rubbers such as polybutadiene and styrene-butadiene rubber, and other elastomers wherein retention of elasticity and inhibition of cross-linking, crazing, discoloration, odor formation and exudation are basic requirements.

Polyesters containing 2-hydroxyphenylthio groups are disclosed in U.S. Pat. No. 3,832,329 as intermediates to be used e.g. for preparing polyurethane polymers, to give reagents useful for imparting chemically-bound plasticization to polymers or to be incorporated into polycarbonates to serve as cross-linking sites.

It is the primary object of this invention to provide a class of polymeric hydroxyphenylthio compounds which exhibit a broad range of improved stabilization performance characteristics.

Various other objects and advantages of this invention will become evident from the following description thereof.

The compounds of this invention correspond to the formula I

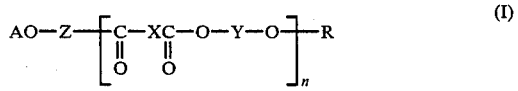

wherein A is alkyl of 1 to 12 carbon atoms, cycloalkyl of 5 to 6 carbon atoms, phenyl, phenyl substituted by alkyl of 1 to 12 carbon atoms or a group of the formula

Q—E—CO— wherein Q is a group of the formula

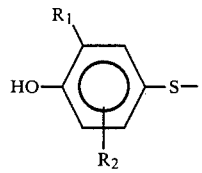

and

E is alkylene of 2 to 6 carbon atoms;

$R_1$ and $R_2$ are independently hydrogen, alkyl of 1 to 18 carbon atoms, cycloalkyl of 5 to 6 carbon atoms, phenyl, phenyl substituted by alkyl of 1 to 12 carbon atoms, aralkyl of 7 to 9 carbon atoms or said aralkyl substituted by alkyl of 1 to 12 carbon atoms;

X which can be the same or different in each repeating unit is alkylene of 2 to 10 carbon atoms which is unsubstituted or substituted by a group Q or is arylene of 6 to 10 carbon atoms;

Y which can be the same or different in each repeating unit is alkylene of 2 to 6 carbon atoms, which is uninterrupted or interrupted by one or two oxygen atoms and is unsubstituted or substituted by a group —O—A;

Z is a direct bond or is alkyleneoxy of 2 to 6 carbon atoms, whereby the oxygen atom is attached to the carbonyl group and the alkylene moiety is uninterrupted or interrupted by one or two oxygen atoms;

R is hydrogen or A;

n is 1 to 100;

with the proviso that at least one of A, X or Y contains a group Q.

$C_1$-$C_{12}$ alkyl radicals are straight-chain or branched alkyl such as methyl, ethyl, n-propyl, isopropyl, n-butyl, sec-butyl, tert-butyl, n-pentyl, tert-pentyl, n-hexyl, 2-ethylhexyl, n-octyl, 1,1,3,3-tetramethylbutyl, decyl or dodecyl. Preferred are $C_1$-$C_8$ alkyl radicals. $R_1$ and $R_2$ as $C_1$-$C_{18}$ alkyl are the same as defined above for $C_1$-$C_{12}$ alkyl and are additionally e.g. tridecyl, tetradecyl, hexadecyl and octadecyl. $C_5$-$C_6$ Cycloalkyl is cyclopentyl or cyclohexyl.

$C_2$-$C_6$ alkylene is for example ethylene, propylene, trimethylene, 2,2-dimethylpropane-1,3-diyl, tetramethylene, pentamethylene or hexamethylene. Alkylene interrupted by one or two oxygen atoms can be for instance 3-oxapentamethylene, 4-oxaheptamethylene or 3,6-di-oxaoctamethylene. X as $C_2$-$C_{10}$ alkylene is the same as defined above for $C_2$-$C_6$ alkylene and is additionally e.g. octamethylene or decamethylene.

When $R_1$ and $R_2$ are aralkyl, they represent for instance benzyl, alpha-methylbenzyl or alpha, alpha-dimethylbenzyl.

X as $C_6$-$C_{10}$ arylene is generally derived from phenyl, tolyl, mesityl, xylyl and 1- and 2-naphthyl.

Particularly interesting compounds are those of the formula 1, wherein A is alkyl of 1 to 8 carbon atoms, phenyl or a group of the formula

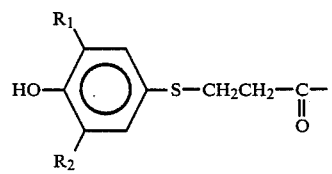

$R_1$ and $R_2$ are independently alkyl of 1 to 8 carbon atoms;

X which can be the same or different in each repeating unit is alkylene of 2 to 6 carbon atoms which is unsubstituted or substituted by a group of the formula

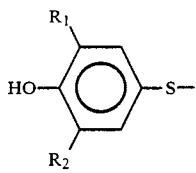

wherein $R_1$ and $R_2$ have the preferred meanings given above or is phenylene.

Y which can be the same or different in each repeating unit is alkylene of 2 to 6 carbon atoms which is unsubstituted or substituted by a group

—O—A wherein

A has the preferred meanings given above or Y is 3-oxapentamethylene;

Z is a direct bond, alkyleneoxy of 2 to 6 carbon atoms or 3-oxapentamethyleneoxy;

R is hydrogen or A, whereby A has the preferred meanings given above;

n is 1 to 50, with the proviso that at least one of A, X or Y contains a group of the formula

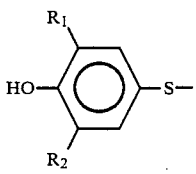

Preferred compounds are those of the formula I wherein A is alkyl of 1 to 8 carbon atoms or a group of the formula

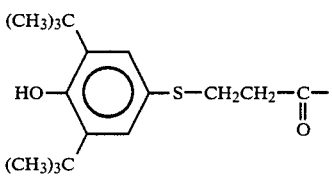

X which can be the same or different on each repeating unit is alkylene of 2 to 6 carbon atoms, 1,2-phenylene or a group of the formula

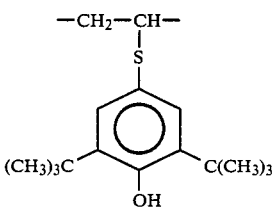

Y which can be the same or different on each repeating unit is alkylene of 2 to 6 carbon atoms, 3-oxapentamethylene or a group of the formula

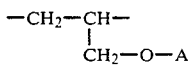

wherein

A has the preferred meaning given above;

Z is a direct bond, ethyleneoxy or 3-oxapentamethyleneoxy;

R is hydrogen or A, whereby A has the preferred meaning given above;

n is 2 to 25, with the proviso that at least one of A, X or Y contain a group of the formula

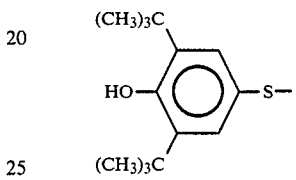

The polymers of this invention can be prepared by the addition of II

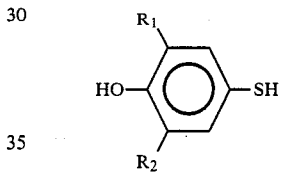

wherein $R_1$ and $R_2$ have the meanings given above, to polymers obtained by reaction of an alcohol with an epoxide and an anhydride, at least one of which containing an α,β-unsaturated carbonyl moiety. A further possibility is that II can be first added to the α,β-unsaturated carbonyl moiety and then polymerized. Therefore II can first be added to at least one of the monomers listed below and then polymerized into the additives of this invention.

The saturated alcohols which can be used include primary and secondary alcohols and phenols containing 1 to 12 carbon atoms, e.g. methanol, ethanol, propyl alcohol, butyl alcohol, cyclohexanol, and the like.

The unsaturated alcohols include e.g. hydroxyethyl acrylate, hydroxypropyl acrylate, hydroxyethyl methacrylate, hydroxyethyl crotonate, and the like.

Suitable saturated epoxides include those containing 2 to 6 carbon atoms, e.g. ethylene oxide, propylene oxide, epichlorohydrin, cyclohexene oxide, butyl glycidyl ether, and the like.

Among the unsaturated epoxides useful herein are e.g. the glycidyl esters of α,β-unsaturated carboxylic acids represented by the formula

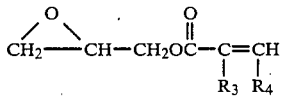

where $R_3$ and $R_4$ are independently methyl or hydrogen. Suitable esters include 2,3-epoxypropyl acrylate, 2,3-epoxypropyl methacrylate and 2,3-epoxypropyl crotonate.

The preferred anhydrides used in the preparation of the polymers of the present invention are those containing 4 to 12 carbon atoms, particularly succinic anhydride, phthalic anhydride, maleic anhydride and the like.

Acid terminated polymers may be reacted with the $\alpha,\beta$-unsaturated epoxides described above and then II added. The hydroxy terminated prepolymers can be transesterified e.g. with acrylate esters and II then added.

A particularly desirable embodiment is to transesterify a compound of the formula

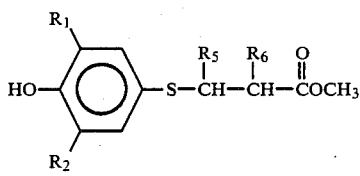

wherein $R_1$ and $R_2$ have the meanings given above, $R_5$ is hydrogen or methyl and $R_6$ is hydrogen, methyl or ethyl, with pre-formed polymers with reactive hydroxyl groups.

All the described reactions, which are condensation, esterification or transesterification reactions can be carried out by methods well known to the skilled in the art.

Compounds of this invention are particularly effective in stabilizing organic materials such as plastics, polymers and resins in addition to mineral and synthetic fluids such as lubricating oils, circulating oils, and the like.

Substrates in which the compounds of this invention are particularly useful are polyolefins such as polyethylene and polypropylene, polystyrene, including impact polystyrene, butadiene rubber, ABS resin, SBR, isoprene, as well as natural rubber.

In general, polymers which can be stabilized include:

1. Polymers of monoolefines and diolefines, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1, for example mixtures of polypropylene with polyisobutylene.

3. Copolymers of monoolefines and diolefines with each other or with other vinyl monomers, such as, for example, ethylene/propylene, propyene/butene-1, propylene/isobutylene, ethylene/butene-1, propylene/-butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or $\alpha$-methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrine homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under 8 with each other or with other unsaturated monomers, such as, for instance, acrylonitrile/butadien, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as a comonomer.

13. Polyphenylene oxides and sulfides, and mixtures of polyphenylene oxides with polystyrene.

14. Polyurethanes which are derived from polyethers, polyesters or polybutadiens with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4,-trimethylhexamethylene terephthalamid or poly-m-phenylene isophthalamide, as well as copolymers thereof with polyethers, such as for instance, with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane]terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Thermosetting acrylic resis, derived from substituted acrylic esters, such as epoxy-acrylates, urethane-acrylates or polyesteracrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymerhomologous manner, such as cellulose acetates, cellulose propionates and cellulose butyrates, or the cellulose ethers, such as methylcellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellithates) and also mixtures of synthetic esters with mineral oils in any weight ratios, which materials may be used as plasticizer for polymers or as textile spinning oils, as well as aqueous emulsions of such materials.

29. Aqueous emulsions of natural or synthetic rubber, e.g. natural latex or latices of carboxylated styrene/butadiene copolymers.

In general, the stabilizers of this invention are employed in from about 0.01 to about 5% by weight of the stabilized composition, although this will vary with the particular substrate and application. An advantageous range is from about 0.05 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain various conventional additives, such as the following.

1. Antioxidants 1.1 Alkylated monophenols, for example,
2,6-di-tert.butyl-4-methylphenol
2-tert.butyl-4,6-dimethylphenol
2,6-di-tert.butyl-4-ethylphenol
2,6-di-tert.butyl-4-n-butylphenol
2,6-di-tert.butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert.butyl-4-methoxymethylphenol 1.2. Alkylated hydroquinones, for example,
2,6-di-tert.butyl-4-methoxyphenol
2,5-di-tert.butyl-hydroquinone
2,5-di-tert.amyl-hydroquinone
2,6-diphenyl-4-octadecyloxyphenol 1.3. Hydroxylated thiodiphenyl ethers, for example
2,2'-thio-bis-(6-tert.butyl-4-methylphenol)
2,2'-thio-bis-(4-octylphenol)
4,4'-thio-bis-(6-tert.butyl-3-methylphenol)
4,4'-thio-bis-(6-tert.butyl-2-methylphenol)

1.4. Alkyliden-bisphenols, for example,
2,2'-methylene-bis-(6-tert.butyl-4-methylphenol)
2,2'-methylene-bis-(6-tert.butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert.butylphenol)
2,2'-ethylidene-bis-(4,6-di-tert.butylphenol)
2,2'-ethylidene-bis-(6-tert.butyl-4-isobutylphenol)
4,4'-methylene-bis-(2,6-di-tert.butylphenol)
4,4'-methylene-bis-(6-tert.butyl-2-methylphenol)
1,1-bis-(5-tert.butyl-4-hydroxy-2-methylphenyl)-butane
2,6-di-(3-tert.butyl-5-methyl-2-hydroxybenzyl)-4-methylphenol
1,1,3-tris-(5-tert.butyl-4-hydroxy-2-methylphenyl)-butane
1,1-bis-(5-tert.butyl-4-hydroxy-2-methylphenyl)-3-n-dodecylmercaptobutane
ethylenglycol-bis-[3,3-bis-(3'-tert.butyl-4'-hydroxyphenyl)-butyrat]
di-(3-tert.butyl-4-hydroxy-b 5-methylphenyl)-dicyclopentadien
di-[2-(3'-tert.butyl-2'-hydroxy-5'methyl-benzyl)-6-tert.butyl-4-methylphenyl]-terephthalate.

1.5. Benzylcompounds, for example,
1,3,5-tri-(3,5-di-tert.butyl-4-hydroxybenzyl)-2,4,6-trimethylbenzene-di-(3,5-di-tert.butyl-4-hydroxybenzyl)-sulfide
3,5-di-tert.butyl-4-hydroxybenzyl-mercapto-acetic acid-isooctyl ester
bis-(4-tert.butyl-3-hydroxy-2,6-dimethylbenzyl)dithiol-terephthalate
1,3,5-tris-(3,5-di-tert.butyl-4-hydroxybenzyl)-isocyanurate
1,3,5-tris-(4-tert.butyl-3-hydroxy-2,6-dimethylbenzyl)-isocyanurate
3,5-di-tert.butyl-4-hydroxybenzyl-phosphoric acid-dioctadecyl ester 3,5-di-tert.butyl-4-hydroxybenzyl-phosphoric acid-monoethyl ester, calcium-salt 1.6. Acylaminophenols, for example,
4-hydroxy-lauric acid anilide
4-hydroxy-stearic acid anilide
2,4-bis-octylmercapto-6-(3,5-tert.butyl-4-hydroxyanilino)-s-triazine
octyl-N-(3,5-di-tert.butyl-4-hydroxyphenyl)-carbaminate 1.7. Esters of β-(3,5-di-tert.butyl-4-hydroxyphenyl)-propionic acid with monohydric or polyhydric alcohols, for example,
methanol
octadecanol
1,6-hexanediol
neopentylglycol
thiodiethyleneglycol
diethyleneglycol
triethyleneglycol
pentaerythritol
tris-hydroxyethyl isocyanurate
di-hydroxyethyl oxalic acid diamide 1.8. Ester of β-(5-tert.butyl-4-hydroxy-3-methylphenyl)propionic acid with monohydric or polyhydric alcohos, for example,
methanol
octadecanol
1,6-hexanediol
neopentylglycol
thiodiethyleneglycol
diethyleneglycol
triethyleneglycol
pentaerythritol
tris-hydroxyethyl isocyanorate
di-hydroxyethyl oxalic acid diamide 1.9. Amides of β-(3,5-di-tert.butyl-4-hydroxyphenyl)-propionic acid for example,
N,N'-di-(3,5-di-tert.butyl-4-hydroxyphenylpropionyl)-hexamethylendiamine
N,N'-di-(3,5-di-tert.butyl-4-hydroxyphenylpropionyl)-trimethylendiamine
N,N'-di-(3,5-di-tert.butyl-4-hydroxyphenylpropionyl)-hydrazine 2. UV absorbers and light stabilisers 2.1. 2-(2'-Hydroxyphenyl)-benztriazoles, for example, the 5'-methyl-, 3',5'-di-tert.butyl-, 5'-tert.butyl-, 5'-(1,1,3,3-tetramethylbutyl)-, 5-chloro-3',5'-di-tert.butyl-, 5-chloro-3'-tert.butyl-5'-methyl-, 3'-sec.butyl-5'-tert.butyl-, 4'-octoxy-, 3',5'-di-tert.amyl-, 3',5'-bis-(α,α-dimethylbenzyl)-derivative.

2.2. 2-Hydroxy-benzophenones, for example, the 4-hydroxy-, 4-methoxy-, 4-octoxy-, 4-decyloxy-, 4-dodecyloxy-, 4-benzyloxy, 4,2',4'-trihydroxy- and 2'-hydroxy-4,4'-dimethoxyderivative.

2.3. Esters of optionally substituted benzoic acids for example, phenyl salicylate, 4-tert.butyl-phenylsalicilate, octylphenyl salicylate, dibenzoylresorcinol, bis-(4-tert.butylbenzoyl)-resorcinol, benzoylresorcinol,3,5-di-tert.-butyl-4-hydroxybenzoic acid 2,4-di-tert.butyl-phenyl ester and 3,5-di-tert.-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5 Nickel compounds, for example, nickel complexes of 2,2'-thiobis-[4-(1,1,3,3-tetramethylbutyl)-phenol], such as the 1:1 or 1:2 complex, optionally with additional ligands such as n-butylamine, triethanolamine or N-cyclohexyl-di-ethanolamine, nickel dibutyldithiocarbamate, nickel salts of 4-hydroxy-3,5di-tert.butylbenzylphosphonic acid monoalkyl esters, such as of the methyl, ethyl or butyl ester, nickel complexes of ketoximes such as of 2-hydroxy-4-methylphenyl undecyl ketonoxime, nickel complexes of 1-phenyl-4-lauroyl-5-hydroxy-pyrazol, optionally with additional ligands.

2.6. Sterically hindered amines, for example
bis-(2,2,6,6-tetramethylpiperidyl)-sebacate
bis-(1,2,2,6,6-pentamethylpiperidyl)-sebacate
n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)hexamethylendiamine and 4-tert.octylamino-2,6-dichloro-1,3,5-s-triazine, tris-(2,2,6,6-tetramethylpiperidyl)-nitrilotriacetate,
tetrakis-(2,2,6,6-tetramethyl-4-piperidyl)-1,2,3,4-butane-tetracarbonic acid, 1,1'(1,2-ethanediyl)-bis-(3,3,5,5-tetramethylpiperazinone).

2.7. Oxalic acid diamides, for example, 4,4'-di-octyloxy-oxanilide, 2,2'-di-octyloxy-5,5'-di-tert.butyl-oxanilide, 2,2'-di-dodecyloxy-5,5'-di-tert.butyl-oxanilide, 2-ethoxy-2'-ethyl-oxanilide, N,N'-bis-(3-dimethylaminopropyl)-oxalamide, 2-ethoxy-5-tert.butyl-2'-ethyloxanilide and its mixture with 2-ethoxy-2'-ethyl-5,4'-di-tert.butyloxanilide and mixtures of ortho-and para-methoxy- as well as of o- and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert.butyl-4-hydroxyphenylpropionyl)hydrazine, 3-salicyloylamino-1,2,4-triazole, bis-benzyliden-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert.butylphenyl)-phosphite, di-isodecylpentaerythritol diphosphite, di-(2,4-di-tert.butylphenyl)pentaerythritol diphosphite, tristearyl-sorbite triphosphite, tetrakis-(2,4-di-tert.butylphenyl-4,4'-biphenylylendiphosphonite.

5. Compounds which destroy peroxide (thiosynergists), for example, esters of β-thio-dipropionic acid, for example the lauryl, stearyl, myristyl or tridecyl esters, mercaptobenzimidazole or the zinc salt of 2-mercaptobenzimidazole, zinc-dibutyl-dithiocarbamate, dioctadecyldisulfide, pentaerythritol-tetrakis-(β-dodecylmercapto)-propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.
8. Nucleating agents, for example, 4-tert.butyl-benzoic acid, adipic acid, diphenylacetic acid.
9. Fillers and reinforcing agents, for example, calcium carbonate, silicates, glass fibres, asbestos, talc, kaolin, mica, barium sulfate, metal oxides and hydroxydes, carbon black, graphite.
10. Other additives, for example plasticizers, lubricants, emulsifiers, pigments, optical brighteners, flame-proofing agents, anti-static agents, blowing agents and thiosynergists such as dilaurylthiodipropionate or distearylthiodipropionate.

Preferred additives to be used together with the compounds of the present invention are costabilizers selected from the group consisting of antioxidants, light stabilizers, metal deactivators, phosphites, phosphonites and thiosynergists.

The following examples illustrate the embodiments of this invention. In these examples, all parts given are by weight unless otherwise specified.

EXAMPLE 1

Poly[1,2-propyleneglycol maleate]

In a 500 ml flask equipped with an acetone-dry ice Dewar condenser, a mixture of 7.41 grams n-butyl alcohol, 49.03 grams maleic anhydride, 29.04 grams propylene oxide, 0.69 gram tetrabutylammonium chloride, and 0.49 gram paramethoxyphenol was heated and held at 75° C. until the acid number was 1.0 mg KOH/gram polymer (approximately 13 hours). IR (1% in chloroform): 1740 cm$^{-1}$ (ester carbonyl), 1640 cm$^{-1}$ (double bond).

EXAMPLE 2

Poly[1,2-propyleneglycol 2-(3,5-di-t-butyl-4-hydroxyphenylthio)succinate]

In a 100 ml flask under nitrogen, a solution of 8.54 grams of the polymer of Example 1 in 2.5 mls toluene was treated with a solution of 11.92 grams 2,6-di-t-butyl-4-mercaptophenol in 25 mls toluene followed by 0.20 gram triethylamine. The solvent was removed in vacuo and the polymer was purified by dry-column chromatography. The IR spectra showed no unsaturation at 1640 cm$^{-1}$.

Anal. Calcd. for $[C_{21}H_{30}O_5S]_n$: S, 7.8. Found: S, 7.5.

EXAMPLE 3

Poly[3-butoxy-1,2-propyleneglycol maleate]

The procedure of Example 1 was repeated using 2.22 grams n-butyl alcohol, 14.71 grams of maleic anhydride, 19.3 grams of butyl glycidyl ether, 0.20 gram tetrabutylammonium chloride, and 0.04 gram paramethoxyphenol until an acid number of 1.7 mg KOH/gram was obtained.

EXAMPLE 4

Poly[3-butoxy-1,2-propyleneglycol 2-(3,5-di-t-butyl-4-hydroxyphenylthio)succinate]

The procedure of Example 2 was repeated using 12.15 grams of the polymer of Example 3, 11.92 grams 2,6-di-t-butyl-4-mercaptophenol, and 1.0 gram triethylamine. The crude polymer was purified by dry-column chromatography. IR (1% solution in chloroform) spectrum showed an ester carbonyl at 1740 cm$^{-1}$ and no unsaturation.

Anal. Calcd. S, 6.6. Found: S, 6.0.

EXAMPLE 5

2-Hydroxyethyl acrylate:succinic anhydride:glycidyl acrylate copolymer

The procedure of Example 1 was repeated using 11.61 grams 2-hydroxyethyl acrylate, 38.44 grams of glycidyl acrylate, 30.02 grams succinic anhydride, 0.40 gram benzyl triethylammonium chloride, and 0.08 gram 2,6-di-t-butyl-4-methylphenol until an acid number of 1.4 mg KOH/gram was obtained. IR (1% solution in chloroform): 1630 cm$^{-1}$ (unsaturation).

EXAMPLE 6

2-Hydroxyethyl 3-(3,5-di-t-butyl-4-hydroxyphenylthio)propanoate:succinic anhydride:glycidyl 3-(3,5-di-t-butyl-4-hydroxyphenylthio)propanoate copolymer The procedure of Example 2 was repeated using 16.01 grams of the polymer of Example 5, 19.07 grams of 2,6-di-t-butyl-4-mercaptophenol and 0.5 gram triethylamine. The crude polymer purified by dry-column chromatography. IR spectrum showed no unsaturation.

Anal.Calcd. S, 7.3. Found: S, 6.9.

EXAMPLE 7

2-Hydroxyethyl acrylate:maleic anhydride:glycidyl acrylate copolymer

The procedure of Example 1 was repeated using 11.6 grams hydroxyethyl acrylate, 38.4 grams glycidyl acrylate, 29.4 grams maleic anhydride, 0.4 gram benzyltriethylammonium chloride, and 0.08 gram 2,6-di-t-butyl-4-methylphenol until an acid number of 0.90 was obtained. IR (1% solution in chloroform): 1735 cm$^{-1}$ (carbonyl), 1640 cm$^{-1}$ (double bond).

EXAMPLE 8

2-Hydroxyethyl 3-(3,5-di-t-butyl-4-hydroxyphenylthio)propanoate:2-(3,5-di-t-butyl-4-hydroxyphenylthio)succinic anhydride:glycidyl 3-(3,5-di-t-butyl-4-hydroxyphenylthio)propanoate copolymer The procedure of Example 2 was repeated using 7.9 grams of the copolymer of Example 7, 16.7 grams of 2,6-di-t-butyl-4-mercaptophenol, and 0.5 gram triethylamine. The crude polymer was purified by dry-column chromatography. The IR spectrum showed no unsaturation.

Anal. Calcd.: S, 9.1. Found: S, 8.7.

EXAMPLE 9

Poly[1,6-hexanediol:neopentylglycol adipate]diol-bis[3-(3,5-di-t-butyl-4-hydroxyphenylthio)-propanoate]

In a 100 ml flask equipped with a short-path distillation head, a mixture of 18.29 gram poly[1,6-hexanediol:neopentylglycol adipate] (OH #122.7), 12.98 grams methyl 3-(3,5-di-t-butyl-4-hydroxyphenylthio)propanoate, and 0.03 gram lithium hydride was heated to 90° C. and held three hours. The pressure was reduced to 25 mm of mercury and heated at 140°-150° C. for three hours. The TLC showed complete disappearance of the starting methyl ester. The polymer was dissolved in toluene, extracted with 1M hydrochloric acid, saturated sodium chloride, dried over sodium sulfate, and the solvent was removed in vacuo.

Anal. Calcd: S, 4.2. Found: S, 4.2.

EXAMPLE 10

Poly[diethyleneglycol o-phthalate]diol-bis[3-(3,5-di-t-butyl-4-hydroxyphenylthio)propanoate]

The procedure of Example 9 was repeated using 33.34 grams poly[di-ethyleneglycol o-phthalate]diol (OH #67.3), 12.98 grams of methyl 3-(3,5-di-t-butyl-4-hydroxyphenylthio)propanoate, and 0.03 grams lithium hydride.

Anal. Calcd.: S, 2.8. Found: S, 2.6.

EXAMPLE 11

Poly[diethyleneglycol adipate]diol-bis[3-(3,5-di-t-butyl-4-hydroxyphenylthio)-propanaote]

The procedure of Example 9 was repeated using 41.63 grams poly[diethyleneglycol adipate]diol (OH #53.9), 12.98 grams methyl 3-(3,5-di-t-butyl-4-hydroxyphenylthio)propanoate and 0.03 gram lithium hydride.

Anal. Calcd.: S, 2.4. Found: S, 2.3.

The residue was recrystallized from a heptane-toluene mixture to give 10.5 grams of a white solid, m.p. 94°–98° C.

EXAMPLE 12

Poly[1,4-tetramethyleneglycol-2(3,5-di-tert-butyl-4-hydroxyphenylthio)succinate]

A mixture of 19.13 grams of dimethyl 2-(3,5-di-tert-butyl-4-hydroxyphenylthio)succinate, 4.51 grams of 1,4-butanediol, and 0.24 gram of tetrabutyl titanate was heated under nitrogen to 130° C. and evolved methyl alcohol collected with an acetone dry ice trap. The pressure was gradually reduced to 0.1 mm Hg and the temperature was raised to 160° C. The product was dissolved in 100 ml hot tetrahydrofuran to which 14 ml of water was added, filtered, the solvent removed in vacuo, and the residue triturated with hexane. The resultant polymer was dried to give 13.6 grams of a white solid, melting at 66°–79° C.

Anal. Calcd. for $[C_{22}H_{32}O_5S]n$: C, 64.7; H, 7.9; S, 7.8. Found: C, 64.9; H, 8.1; S, 7.8.

EXAMPLE 13

Stabilization of impact polystyrene

In the laboratory procedure utilized herein, a solution of eight weight percent polybutadiene rubber (Firestone-DIENE 55) dissolved in styrene monomer was prepared on a roller mill. The indicated amount of stabilizer was also introduced at this point. 500 ppm of zinc stearate was added to aid in removing the sample from the bottle after the polymerization. The bottle was screwed into the polymerization apparatus which was equipped with a double helical ribbon stirrer. Since most commercial IPS bulk polymerizations are thermally initiated processes, no initiator was used in the laboratory process. A nitrogen atmosphere was established and then the reactor was heated to 121° C. within ½ hour. Heating was continued at 121° C. with efficient stirring until there was a 30 to 35% monomer conversion (2½ hours). The stirring rate was controlled to yield a two to four μm rubber particle size. The bottles were removed from the polymerization apparatus, blanketed with nitrogen, capped and then placed in a fluidized bed sand bath to complete the polymerization. The bottles were heated in the bath in the following fashion: one hour at 100° C. to equilibrate the temperature, one hour to reach 140° C. and then an additional eight hours with the temperature increasing at the rate of 10° C. per hour to a maximum of 220° C. After the resin had cooled, the bottle was broken and the glass was removed. The average weight of the polymer block was slightly over 600 grams. The block was then placed into a vacuum oven at 200° C. and a vacuum of 1 mm applied as the polymer was heated for 45 minutes in order to remove all volatiles. The block was removed from the oven, immediately placed in a heated (205° C.) hydraulic press and then pressed into a thick slab between two sheets of aluminum foil (three minutes heating, five minutes in a cold press). The slab was split with a band saw and the pieces were granulated.

All batches were extruded at 205° C. and then pelletized. The pellets were compression molded at 205° C. into 125 mil (3,2 mm) tensile bars. The bars were then aged at 150° C. on glass plates placed on rotating shelves in a forced air oven. The specimen yellowness index was determined on the bars at various intervals according to ASTM D-1925-63T. Correspondingly, the bars were periodically measured for percent elongation in the Instron Tensile Testing Apparatus (Instron Engineering Corporation, Massachusetts) at a pull rate of 5 mm/minute according to ASTM D-638.

| Oven Aged Samples at 150° C. | | | | | |
|---|---|---|---|---|---|
| | | Hours at 150° C. | | | |
| Additive | Conc. | 0 | ½ | 1 | 1½ | 2 |
| % Elongation | | | | | | |
| None | — | 33 | 7 | 7 | 3 | 3 |
| Compound of Example 6 | 0.1% | 45 | 52 | 48 | 19 | — |
| Compound of Example 8 | 0.1% | 61 | 17 | — | 10 | 9 |
| Yellowness Index | | | | | | |
| None | — | 7 | 18 | 30 | 38 | 43 |
| Compound of Example 6 | 0.1% | −2 | 4 | 8 | 10 | — |
| Compound of Example 8 | 0.1% | 4 | 8 | 17 | 20 | 22 |

EXAMPLE 14

Stabilization of polypropylene (Light stability)

Unstabilized polypropylene powder (Hercules Profax 6501) was thoroughly blended with 0.2%, by weight, of additive. The blended materials were then milled on a two roll mill at 182° C. for 5 minutes, after which time the stabilized polypropylene was sheeted from the mill and allowed to cool. The milled polypropylene was then cut into pieces and compression molded on a hydraulic press at 220° C. (175 psi) into 5 mil (0.13 mm) films. The sample was exposed in a fluorescent sunlight/black light chamber until failure. Failure was determined when the films showed the first signs of decomposition (e.g. cracking or brown edges).

| Additive | Hours to failure |
|---|---|
| None | 200–300 |
| Compound of Example 2 | 380 |
| Compound of Example 4 | 410 |
| Compound of Example 6 | 450 |
| Compound of Example 8 | 360 |
| Compound of Example 9 | 350 |
| Compound of Example 10 | 400 |

-continued

| Additive | Hours to failure |
|---|---|
| Compound of Example 11 | 390 |

EXAMPLE 15

Stabilization of polypropylene (Oxidation stability)

The oxidation stability of milled polypropylene containing 0.2% of additive as well as that of the synergized formulation containing 0.1% of additive in the presence of 0.3% distearylthiodipropionate (DSTDP) on plaques of 25 mil (0.64 mm) thickness was determined by exposing said plaques to air in a forced draft oven at 150° C. The plaques were considered to have failed on showing the first signs of decomposition (e.g., cracking or brown edges).

| | Time to failure (hrs.) | |
|---|---|---|
| Additive | 0.2% Additive | 0.1% Additive + 0.3% DSTDP |
| Base Resin | <20 | <20 |
| Compound of Example 2 | 330 | 580 |
| Compound of Example 4 | 410 | 570 |
| Compound of Example 6 | 170 | 240 |
| Compound of Example 8 | 130 | 320 |
| Compound of Example 9 | 120 | 190 |
| Compound of Example 10 | 30 | 160 |
| Compound of Example 11 | 30 | 150 |

Examples 13–15 thus indicate the significantly better performance of the instant compounds as compared to the base resin.

Summarizing, it is seen that this invention provides a group of compounds which have superior stabilizing activity in a variety of organic materials. Variations may be made in proportions, procedures and materials without departing from the scope of the invention as defined by the following claims.

What is claimed is:

1. A compound of the formula

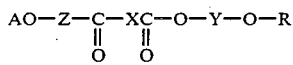

wherein A is alkyl of 1 to 12 carbon atoms, cycloalkyl of 5 to 6 carbon atoms, phenyl, phenyl substituted by alkyl of 1 to 12 carbon atoms or a group of the formula

wherein Q is a group of the formula

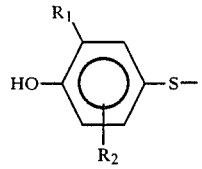

and

E is alkylene of 2 to 6 carbon atoms;

$R_1$ and $R_2$ are independently hydrogen, alkyl of 1 to 18 carbon atoms, cycloalkyl of 5 to 6 carbon atoms, phenyl, phenyl substituted by alkyl of 1 to 12 carbon atoms, aralkyl of 7 to 9 carbon atoms or said aralkyl substituted by alkyl of 1 to 12 carbon atoms;

X which can be the same or different in each repeating unit is alkylene of 2 to 10 carbon atoms which is unsubstituted or substituted by a group Q or is arylene of 6 to 10 carbon atoms;

Y which can be the same or different in each repeating unit is alkylene of 2 to 6 carbon atoms, which is uninterrupted or interrupted by one or two oxygen atoms and is unsubstituted or substituted by a group —O—A;

Z is a direct bond or is alkyleneoxy of 2 to 6 carbon atoms, whereby the oxygen atom is attached to the carbonyl group and the alkylene moiety is uninterrupted or interrupted by one or two oxygen atoms;

R is hydrogen or A;

with the proviso that at least one of A, X or Y contains a group Q.

2. A composition of matter comprising an organic material subject to oxidative, thermal and actinic degradation stabilized with an effective stabilizing amount of a compound of claim 1.

3. The composition of claim 2 containing additionally a costabilizer selected from the group consisting of antioxidants, light stabilizers, metal deactivators, phosphites, phosphonites and thiosynergists.

4. The composition of claim 2, wherein the organic material is a synthetic polymer.

5. The composition of claim 4, wherein said polymer is selected from the group consisting of polyolefins, impact polystyrene, butadiene rubber, acrylonitrile/butadiene/styrene, styrene/butadiene rubber.

6. A method for stabilizing an organic material against oxidative, thermal and actinic degradation which comprises incorporating into said organic material an effective stabilizing amount of a compound of claim 1.

* * * * *